United States Patent [19]

Fahey et al.

[11] 4,115,470

[45] Sep. 19, 1978

[54] ORGANOPHOSPHORUS NICKEL COMPLEXES AND USE THEREOF

[75] Inventors: Darryl R. Fahey; John E. Mahan, both of Bartlesville, Okla.

[73] Assignee: Phillips Petroleum Company, Bartlesville, Okla.

[21] Appl. No.: 858,760

[22] Filed: Dec. 8, 1977

Related U.S. Application Data

[62] Division of Ser. No. 684,350, May 7, 1976.

[51] Int. Cl.$^2$ .............................................. C07C 3/10
[52] U.S. Cl. ...................... 260/683.15 D; 260/439 R; 260/666 B
[58] Field of Search ................... 260/683.15 D, 439 R

[56] References Cited

U.S. PATENT DOCUMENTS

| | | | |
|---|---|---|---|
| 3,102,899 | 9/1963 | Cannell | 260/439 R |
| 3,808,246 | 4/1974 | Fahey | 260/439 R |
| 3,818,063 | 6/1974 | Fahey | 260/439 R |
| 3,903,120 | 9/1975 | Shook et al. | 260/439 R |
| 3,907,923 | 9/1975 | Yoo | 260/683.15 D |
| 4,000,211 | 12/1976 | Smith et al. | 260/683.15 D |

Primary Examiner—C. Davis

[57] ABSTRACT

The preparation and use of bis(μ-diphenylphosphido)-tris(triethylphosphine)dinickel and tris(triethylphosphine)(triphenylphosphine)nickel is disclosed.

6 Claims, No Drawings

ORGANOPHOSPHORUS NICKEL COMPLEXES AND USE THEREOF

This application is a divisional application of application Ser. No. 684,350, filed May 7, 1976, now indicated as allowable.

This invention relates to organo-nickel complexes. In another aspect this invention relates to organophosphorus nickel complexes and their use.

Methods are known in the art for the dimerization of olefinic hydrocarbons in the presence of a catalyst system containing a nickel complex. Dimerization of propylene and other lower monoolefins continues to be of interest in the synthesis of monomers for addition polymerization, as intermediates in alcohol production by the oxo process, and as intermediates in the manufacture of plasticizers, lube additives, monomers for condensation polymerization, detergent base materials, improved motor fuel and the like. This continuing interest has established a need in the art for improved nickel complex dimerization catalysts. The extent of the dimerization, as well as stability of the resulting catalyst, is greatly dependent upon the character of the components employed to produce the catalyst system. In general, substantial variations in resulting dimer product types, catalyst stability, and olefin conversion are encountered when the character of the catalyst complex is varied.

It is an object of the present invention to provide a novel organophosphorus nickel complex which can be employed in the oligomerization of monoolefins or conjugated dienes.

A further object of the present invention is to provide another novel organophosphorus nickel complex which can be employed to prepare the previously-mentioned nickel complex.

A further object of the present invention is to provide processes for preparing both nickel complexes.

A still further object is to provide processes for oligomerizing monoolefins or conjugated dienes employing said first-mentioned novel organophosphorus nickel complex.

The first-mentioned novel organophosphorus complex of this invention is bis($\mu$-diphenylphosphido)tris(triethylphosphine)dinickel, hereinafter referred to for convenience as $Ni_2(\mu\text{-}PPh_2)_2(PEt_3)_3$.

The second-mentioned novel organophosphorus complex of this invention is tris(triethylphosphine)(triphenylphosphine)nickel(0), hereinafter referred to for convenience as $Ni(PEt_3)_3(PPh_3)$.

The organophosphorus nickel complexes of this invention, like many of the compounds employed in preparing them, are sensitive to oxygen and/or water to varying degrees. Therefore the preparation and use of these complexes should be conducted under an inert atmosphere, for example in a recirculating-atmosphere drybox providing an inert atmosphere.

One method of preparing $Ni(PEt_3)_3(PPh_3)$ according to this invention involves reacting suitable amounts of tetrakis(triethylphosphine)nickel(0) and triphenylphosphine in a suitable diluent under reaction conditions that will yield said $Ni(PEt_3)_3(PPh_3)$. While any suitable temperature can be employed, in general the temperature will be in the range of about $-50°$ to about $100°$ C. Preferably the reaction temperature is in the range of about $-20°$ to about $50°$ C. Any suitable molar ratio of triphenylphosphine to $Ni(PEt_3)_4$ can be employed, but in general this ratio will be in the range of about 0.1:1 to about 1:0.1, and preferably in the range of about 0.5:1 to about 1:0.5. Any pressure is satisfactory that will essentially maintain the diluent in the liquid phase at the reaction temperature. In general the pressure will be in the range of about 5 to about 1000 psia, and atmospheric pressure is preferred. Any diluent can be employed that does not prevent the formation of $Ni(PEt_3)_3(PPh_3)$. Suitable diluents include, for example, unsubstituted ethers, aromatic hydrocarbons, aliphatic hydrocarbons, and mixtures of any two or more thereof. Typical examples of diluents include diethyl ether, p-dioxane, tetrahydrofuran, benzene, toluene, pentane, hexane, octane, and mixtures of two or more thereof. Any suitable time for reaction can be employed, but of course it will be dependent upon the conditions employed. The reaction time is generally in the range of about 1 minute to about 10 hours, and preferably in the range of about 0.1 hour to about 2 hours.

The $Ni(PEt_3)_3(PPh_3)$ can then be recovered and purified using techniques conventionally employed by those skilled in the art for recovering and purifying products contained in a diluent, i.e., precipitation, filtration and washing; or evaporation in vacuo, separation of impurities by chromatography, and recrystallization.

The product $Ni(PEt_3)_3(PPh_3)$ in a suitable diluent is converted to the novel complex $Ni_2(\mu\text{-}PPh_2)_2(PEt_3)_3$. Any suitable temperature can be employed. Generally, temperatures in the range of about 25° to about 175° C. are satisfactory. It is now preferred that temperatures be in the range of about 60° to about 130° C. Any diluent can be employed that does not prevent the formation of the $Ni_2(\mu\text{-}PPh_2)_2(PEt_3)_3$. Suitable diluents include for example, unsubstituted ethers, aromatic hydrocarbons, aliphatic hydrocarbons, and mixtures of any two or more thereof. Typical examples of such diluents include diethyl ether, p-dioxane, tetrahydrofuran, benzene, toluene, pentane, hexane, octane and mixtures of two or more thereof. The preferred diluents are aliphatic hydrocarbons containing 5 to 10 carbon atoms. Any pressure is satisfactory that will essentially maintain the diluent in the liquid phase at the reaction temperature. In general the pressure will be in the range of about 5 to about 1000 psia, and atmospheric pressure is preferred. Any suitable time for the reaction can be employed, but of course it will be dependent upon the conditions employed and the yield sought. The reaction time will generally be in the range of about 0.1 hour to about 100 hours, preferably in the range of about 1 to about 6 hours.

Another process for preparing $Ni_2(\mu\text{-}PPh_2)_2(PEt_3)_3$ comprises reacting a mixture of suitable amounts of $Ni(PEt_3)_4$ and pentafluorophenyldiphenylphosphine in a suitable diluent. Again the reaction pressure is any pressure that will essentially maintain the diluent in the liquid phase at the reaction temperature. In general the pressure will be in the range of about 5 to about 1000 psia, and atmospheric pressure is preferred. Any suitable reaction temperature can be employed. Generally temperatures in the range of about $-10$ to about $150°$ C., preferably in the range of about 0° to about 60 are satisfactory. Any diluent can be employed that does not prevent the formation of $Ni_2(\mu\text{-}PPh_2)_2(PEt_3)_3$. Suitable diluents include those examples set forth in the process described in the preceding paragraph. Particularly preferred diluents are aliphatic unsubstituted ethers. The molar ratio of pentafluorophenyldiphenylphosphine to $Ni(PEt_3)_4$ is generally in the range of about 0.1:1 to 1:0.1 and preferably is about 0.5:1 to 1:0.5. Again the time for this reaction will of course be dependent upon the conditions employed and the yield sought. The reaction time is generally in the range of about 0.1 hour to about 100 hours, preferably in the range of about 1 to about 6 hours.

Still another process for preparing $Ni_2(\mu\text{-}PPh_2)_2(PEt_3)_3$ comprises reacting suitable amounts of trans-dichlorobis(triethylphosphine)nickel(II) with lithium diphenylphosphide etherate in a suitable diluent under suitable reaction conditions to yield a reaction product which is then reacted in a suitable diluent with a suitable amount of $Ni(PEt_3)_4$. Generally the mole ratio of lithium diphenylphosphide etherate to trans-dichlorobis(triethylphosphine)nickel(II) is in the range of about 1.5:1 to about 2.5/1, preferably about 2:1. Any suitable mole ratio of $Ni(PEt_3)_4$ to trans-dichlorobis(triethylphosphine)nickel(II) can be employed but, in general this ratio will be in the range of about 0.5:1 to about 10:1, preferably about 1:1 to 1.5:1. While any suitable reaction temperature can be employed, in general the reactions are conducted in the temperature range of about $-50°$ to about $150°$ C., preferably about $0°$ to about $25°$ C. Any diluent can be employed that does not prevent the formation of $Ni_2(\mu\text{-}PPh_2)_2(PEt_3)_3$. The preferred diluents are ethers or ether-hydrocarbon admixtures. Unsubstituted aliphatic ethers or combination thereof with aliphatic hydrocarbons are especially preferred. Typical examples include diethyl ether, p-dioxane, tetrahydrofuran, or combinations of such ethers with hydrocarbons such as benzene, toluene, pentane, hexane and octane. Again in this process the pressure is any pressure that will essentially maintain the diluent in the liquid phase at the reaction temperature. In general the pressure will be in the range of about 5 to about 1000 psia and atmospheric pressure is preferred. The reaction time will of course depend upon the conditions employed and the yield sought; however, the reaction time is generally in the range of about 0.1 hour to about 100 hours, preferably in the range of about 0.5 to about 6 hours.

The product, $Ni_2(\mu\text{-}PPh_2)_2(PEt_3)_3$, produced by any of the three processes just described can be recovered and purified using techniques conventionally employed by those skilled in the art. For this reason it is convenient that a diluent be selected in which the dinickel complex is relatively insoluble at a temperature on the order of about $-20°$ to about $-80°$ C. Alternatively it is convenient to employ a diluent that is sufficiently volatile that the dinickel complex can be isolated by evaporating the reaction mixture in vacuo.

The novel compound $Ni_2(\mu\text{-}PPh_2)_2(PEt_3)_3$ is useful in the oligomerization of monoolefins or conjugated dienes.

In accordance with the process for oligomerizing monoolefins, a catalyst system is employed comprising $Ni_2(\mu\text{-}PPh_2)_2(PEt_3)_3$ and at least one organoaluminum compound represented by the formula $R_nAlX_{3-n}$, wherein each R is a hydrocarbyl radical having from 1 to 20 carbon atoms; each X is a halogen; and n is 1, 1.5 or 2.

Some specific examples of organoaluminum components of the catalyst system are: methylaluminum dichloride, dimethylaluminum chloride, diethylaluminum bromide, ethylaluminum dibromide, vinylaluminum diiodide, dibutylaluminum chloride, phenylaluminum dibromide, dibenzylaluminum chloride, 4-tolylaluminum dichloride, dodecylaluminum dibromide, methylaluminum sesquichloride, and the like and mixtures thereof. Presently preferred aluminum compounds are organoaluminum halides particularly those containing hydrocarbon radicals having 1 to 6 carbons, such as methylaluminum sesquichloride.

The catalyst components can be combined in any suitable proportions. Generally they are combined in proportions in a range of 0.5:1 to about 20:1 moles of an organoaluminum halide per mole of nickel complex. Catalyst poisons in the system can be scavenged by employing even greater proportions of the organoaluminum compound.

The catalyst system is prepared by combining the first and second components of the catalyst under suitable conditions of time and temperature which permit the active catalyst to be formed. The two components of the catalyst system can be mixed under any suitable temperature. Generally the temperature at which the catalyst is prepared is in the range of about $-80°$ to about $100°$ C. for a period of time ranging from a few seconds up to several hours in the presence of a diluent in which both of the two components are at least partially soluble. Any diluent is suitable that is an inert liquid under the reaction conditions. Examples of suitable solvents or diluents are benzene, cyclohexane, chlorobenzene, methylene chloride, ethylene chloride, and the like. However, halogenated diluents are preferred. The forming of the catalyst system by admixing the two components is generally carried out in an inert atmosphere and in the substantial absence of air or moisture. After the catalyst system is formed, it need not be isolated but can be added directly to the reaction zone as a solution or suspension in its preparation medium. If desired, the components used to form the catalyst system can be separately added, in any order, to the reaction zone either in the presence or absence of the feed olefin.

Any suitable monoolefin can be oligomerized employing the just-described catalyst system. Examples of suitable monoolefins include, for example, ethylene, propylene, butene-1, butene-2, pentene-1, pentene-2, cyclopentene, cyclohexene, 3,4,5-trimethylcyclohexene, 3-methylbutene-1, cycloheptene, hexene-2, heptene-1, cyclooctene, 4,4-dimethylheptene-2, decene-1, dodecene-1, and the like, and mixtures of any two or more thereof. The preferred monoolefins are those having from 2 to 12 carbon atoms and no branching on a doubly bonded carbon. Especially preferred at the present time is propylene.

The oligomerization of the monoolefin or mixture of monoolefins can take place at any suitable temperature. Generally the temperature is within the range of $-80°$ to about $200°$ C., and preferably within the range of $-10°$ to about $50°$ C. The reaction is carried out with the diluent in the liquid phase. Also any suitable pressure can be employed. Normally, it is desirable to carry out the dimerization reaction under pressures ranging from about 0 psig up to about 2000 psig and preferably 20-50 psig. The oligomerization can be carried out in the presence of a diluent such as that used for the catalyst preparation if desired. The time of contact of the olefin with the catalyst for the oligomerization of the olefin will vary depending upon the desired degree of conversion but generally will be within the range from about 0.1 minute to about 20 hours, preferably 5 to 120 minutes. The proportion of nickel complex to olefin feed in the reaction zone will generally be within the range of about 0.00001 to about 0.1 mole of nickel complex per mole of olefin feed.

Any conventional contacting technique can be utilized for the olefin oligomerization and batchwise or continuous operations can be utilized. After the desired degree of conversion of the olefin to the dimer, the products so formed can be separated and isolated by conventional means such as by fractionation, crystallization, adsorption, and the like. The unconverted feed material can be recycled to the reaction zone. If desired, the catalyst can be destroyed by treatment with suitable deactivating agents such as water or alcohol, prior to the separation of the products.

In accordance with this invention conjugated dienes can also be oligomerized employing $Ni_2(\mu\text{-}PPh_2)_2(PEt_3)_3$. Any suitable conjugated diene or mixture of suitable conjugated dienes can be oligomerized by the process. Generally the oligomerization employs at least one conjugated diene having from 4 to 8 carbon atoms per molecule. Examples of such dienes include 1,3-butadiene, 2,3-dimethylbutadiene, isoprene, piperylene, 1,3-heptadiene, 2,4-heptadiene, 1,3-hexadiene, 2,3-dimethylpiperylene, and the like, and mixtures of any two or more thereof. The process involves contacting said at least one conjugated diene with a catalyzing amount of $Ni_2(\mu\text{-}PPh_2)_2(PEt_3)_3$ in a suitable diluent under reaction conditions conducive to oligomerization. Generally the temperature of oligomerization is in the range of from about 100° to about 175° C., preferably in the range of about 115° C. to about 150° C. The reaction is carried out with the diluent in the liquid phase. The pressure is generally in the range of about 0 to about 2000 psig, preferably about 20 to about 50 psig.

Any suitable diluent can be employed that does not interfere with the oligomerization. Examples of suitable diluents include alkanes, for example, hexane, heptane and octane; cycloalkanes, for example, cyclohexane and methylcyclohexane; aromatic hydrocarbons, for example, benzene and toluene; unsubstituted ethers, for example, diethyl ether, p-dioxane, and tetrahydrofuran; cyclic polyenes, for example, cyclooctadiene and cyclododecatriene; and mixtures of any two or more thereof. Generally the time for the reaction is in the range of about 0.5 to about 6 hours, preferably about 1 to about 3 hours.

Without further elaboration, one skilled in the art using the preceding disclosure should be able to utilize the present invention to its fullest extent. The following preferred specific embodiments are, therefore, to be construed as merely illustrative, and not limitative of the remainder of the specification and claims in any way whatsoever.

Unless it is indicated as otherwise the work described in the following examples was done at atmospheric pressure in a recirculating-atmosphere drybox providing an argon atmosphere.

EXAMPLE I

Preparation of Tris(triethylphosphine)(triphenylphosphine)nickel(0) from $Ni(PEt_3)_4$ The tris(triethylphosphine)(triphenylphosphine)nickel(0), represented by the formula $Ni(PEt_3)_3(PPh_3)$, was prepared by the following procedure: A 5 ml solution of 0.52 g (2.0 mmols) of triphenylphosphine in ether was slowly added to 0.83 g (1.6 mmols) of tetrakis(triethylphosphine)nickel(0), represented by the formula $Ni(PEt_3)_4$, in 5 ml of ether at 25° C. On standing, 0.19 g of orange-red crystalline tris(triethylphosphine)(triphenylphosphine)nickel(0) precipitated. These crystals were removed by suction filtration, washed with ether and dried in vacuo. Concentration of the filtrate under reduced pressure and cooling to −30° C. resulted in an additional 0.78 g of orange-red crystals to give a total yield of 0.97 g (90% of theory); m.p. 95.5° -97° C.; ir (Nujol) 2900 vs, 1585 w, 1450 s, 1425 m, 1405 w, 1375 m, 1260 w, 1240 w, 1220 vw, 1080 w, 1040 w, 1030 m, 1000 vw, 985 vw, 965 vw, 757 m, 743 s, 717 m, 695 s cm$^{-1}$; NMR ($C_6D_6$) > 7.7 (v br, 6), 7.15 (m, >9 due to $CD_5H$ impurity), 1.58 (q, 18, J = 6.8 Hz), 1.05 (t, 27, J = 6.8 Hz). Anal. Calcd. for $C_{36}H_{60}NiP_4$: C, 64.01; H, 8.95; Ni, 8.69; P, 18,35. Found: C, 63.89; H, 9.28; Ni, 8.83; P, 18.37.

EXAMPLE II

Preparation of $Ni_2(\mu\text{-}PPh_2)_2(PEt_3)_3$ from $Ni(PEt_3)_3(PPh_3)$

A closed vial containing 1.36 g (2.0 mmol) of tris(triethylphosphine)(triphenylphosphine)nickel(0), having the formula $Ni(PEt_3)_3(PPh_3)$, in 20 ml of hexane was suspended in a refluxing benzene bath. In less than about 10 minutes the orange colored solution had turned dark green. After 5 hours the solution was cooled to −78° C. and lustrous dark green crystals precipitated. The crystals were removed by suction filtration, washed with cold hexane, and dried in a stream of argon to yield 0.39 g (0.46 mmol) of $Ni_2(\mu\text{-}PPh_2)_2(PEt_3)_3$; m.p. 193°-195° C. (dec.); ir (Nujol) 3040 w, 2910 vs, 2880 vs, 1580 m, 1455 m, 1425 m, 1375 m, 1150 w, 1075 w, 1055 w, 1030 s, 1000 w, 767 s, 763 s, 748 ms, 736 s, 724 m, 707 s, 700 vs, 694 s cm$^{-1}$; NMR ($C_6D_6$) δ 7.9 (v br, 6.6), 7.15 (v br, 17.4 — includes $C_6D_5H$ impurity), 1.00 (v br, 45).

Anal. Calcd. for $C_{42}H_{65}Ni_2P_5$: C, 59.89; H, 7.78; Ni, 13.94.

Found: C, 59.54; H, 7.78; Ni, 13.88.

EXAMPLE III

Preparation of $Ni_2(\mu\text{-}PPh_2)_2(PEt_3)_3$ from $C_6F_5PPh_2$ and $Ni(PEt_3)_4$ A solution of 1.06 g (2.0 mmols) of tetrakis(triethylphosphine)nickel(0), represented by the formula $Ni(PEt_3)_4$, in 5 ml of ether was treated with 0.70 g (2.0 mmols) of pentafluorophenyldiphenylphosphine, represented by the formula $C_6F_5PPh_2$, in 5 ml of ether at about 0° C. The mixture turned brown and was warmed to 25° C. for 5-10 minutes before cooling to −78° C. The solution was then green but no crystals had formed and the mixture was evaporated to dryness under reduced pressure to yield a dark green gum. This residue was extracted with hexane, and the extract was chromatographed on a column of neutral alumina. A green colored product was eluted from the column with 5% ether in hexane and purification of this material by recrystallization from hexane at −72° C. gave 0.07 g (8% of theory) of $Ni_2(\mu\text{-}PPh_2)_2\text{-}(PEt_3)_3$. The product of this run melted at 189°-190° C. (dec.) and exhibited an infrared (ir) spectrum identical to that of the product isolated in Example II.

EXAMPLE IV

Preparation of $Ni_2(\mu\text{-}PPh_2)_2(PEt_3)_3$ from $NiCl_2(PEt_3)_2$ and $LiPPh_2.Et_2O$ A 25 ml ether solution containing 1.83 g (5.0 mmols) of transdichlorobis(triethylphosphine)nickel(II), represented by the formula $NiCl_2(PEt_3)_2$, was treated with 2.66 g (10.0 mmols) of lithium diphenylphosphide etherate, represented by the formula $LiPPh_2 \cdot Et_2O$, in 30 ml of ether at about 0° C. The solution immediately turned dark green. Ater 15 minutes 2.66 g (5.0 mmols) of tetrakis(triethylphosphine)nickel(0), $Ni(PEt_3)_4$, was added to the stirred solution and the mixture was allowed to stand at 25° C. for 1 hour before evaporating the solution to dryness under reduced pressure. The residue was extracted with about 200 ml of hexane and the extract was filtered before chilling to −72° C. The precipitated dark green crystals of $Ni_2(\mu\text{-}PPh_2)_2(PEt_3)_3$ were removed by suction filtration, washed with hexane and dried in vacuo to give 1.54 g of product melting at 194° C. (dec.). Four additional crops of green crystals were obtained from the above filtrate to increase the yield to 2.86 g (68% of theory).

A final recrystallization of the total product sample from ether at −30° C. gave 1.95 g of green crystals melting at 194°–195° C. (dec.). An additional 0.34 g of product was obtained from the filtrate. The infrared spectrum (Nujol) was identical to that exhibited by the $Ni_2(\mu\text{-}PPh_2)_2(PEt_3)_3$ product obtained in Example II.

EXAMPLE V

Monoolefin Oligomerization Employing $Ni_2(\mu\text{-}PPh_2)_2(PEt_3)_3$

A predried nine ounce beverage bottle equipped with a magnetic stirring bar was charged in a dry box with 0.04 g (0.05 mmol) of $Ni_2(\mu\text{-}PPh_2)_2(PEt_3)_3$, 20 ml of chlorobenzene and then capped. The capped bottle was removed from the dry box and flushed successively for one hour periods, with argon and propylene before chilling the stirred solution for 5 minutes in an ice-salt-water bath. The chilled bottle was pressured to 30 psig with propylene and then vented to 5 psig. A 0.70 ml (equivalent to 0.70 mmol methylaluminum sesquichloride) aliquot of a 1 molar solution of methylaluminum sesquichloride in chlorobenzene was added by syringe and the solution immediately turned from green to brown. The pressure was increased to 30 psig with propylene and maintained at this pressure in the cold bath and one hour later the propylene was shut off, the bottle vented and 10 ml of saturated aqueous sodium chloride solution was added. The aqueous phase was separated, extracted with 5 ml of chlorobenzene and the chlorobenzene extract was combined with the chlorobenzene phase from the reaction mixture. The combined chlorobenzene phases were dried over anhydrous magnesium sulfate, filtered and distilled to recover 43.4 g of propylene dimers collected over the temperature range of 60°–68° C.

Skeletal characterization of the propylene dimers was carried out by hydrogenating a 2.0 g sample of the above isolated propylene dimers over 0.1 g of platinum oxides under 50–90 psig of hydrogen for a period of 3 hours. The hydrogenated product mixture was analyzed by gas-liquid partition chromatography on a 20 ft. by 0.125 in. isoquinoline column at a 25° C. oven temperature. The composition in area percent of the hydrogenated product was as follows: 19% 2,3-dimethylbutane, 68% 2-methylpentane and 13% n-hexane.

EXAMPLE VI

Diene Oligomerization Employing $Ni_2(\mu\text{-}PPh_2)_2(PEt_3)_3$

A predried six ounce aerosal compatibility bottle equipped with a magnetic stirring bar was charged in a dry box with 0.17 g (0.20 mmol) of $Ni_2(\mu\text{-}PPh_2)_2(PEt_3)_3$, 10 ml of benzene and then capped. The capped bottle was removed from the dry box and 20.65 g (0.382 mol) of 1,3-butadiene was added. The bottle was heated in an oil bath as the contents were magnetically stirred. The temperature was gradually increased. After about one hour at a temperature of about 80° C. the pressure in the bottle was 93 psig. The absence of any observed pressure drop was taken to indicate that no significant reaction had yet occurred. After heating for about 30 more minutes the temperature was about 118° C. and the pressure in the bottle about 160 psig. After one hour at this temperature, the pressure had fallen to 143 psig. The reaction mixture was then cooled. After being allowed to set at room temperature over the weekend the reaction mixture was heated to about 120° C. After about an hour at this temperature the pressure in the bottle had dropped from 110 psig to 20 psig. The reaction mixture was then cooled and an additional 19.23 g (0.356 mol) of 1,3-butadiene was added. The reaction mixture was then reheated to 120° C. After about 2 more hours at 120° C., the pressure again decreased to about 20 psig. The reaction mixture was then again cooled and a further 29.67 g (0.549 mol) of 1,3-butadiene was added. After heating this mixture for about two more hours at 120° C. the pressure dropped to about 38 psig. The reaction was then terminated although the solution still retained its homogeneous dark green appearance. The mixture was then exposed to air to destroy the catalyst and filtered. The filtrate was distilled to afford 28.7 g of 1,5-cyclooctadiene, 5.7 g of 1,5,9-cyclododecatriene, and other products.

The terms and expressions employed in this disclosure are used as terms of description and are not intended to be unduly limiting. There is no intention in the use of such terms and expressions of excluding any equivalents of features shown and described or portions thereof. Further, it should be recognized that various modifications are possible within the scope of the following claims.

What is claimed is:

1. A process for oligomerizing monoolefins comprising contacting under suitable reaction conditions at least one said monoolefin with a catalyzing amount of a catalyst system comprising at least one organoaluminum compound $R_nAlX_{3-n}$ wherein each R is a hydrocarbyl radical having from 1 to 20 carbon atoms, each X is a halogen, and n is 1, 1.5, or 2; and bis($\mu$-diphenylphosphido)tris(triethylphosphine)dinickel wherein the mole ratio of said organoaluminum compound to said dinickel complex is in the range of about 0.5:1 to about 20:1.

2. A process according to claim 1 wherein any branched monoolefin that is dimerized is a branched monoolefin in which the branching is not on a doubly bonded carbon.

3. A process according to claim 2 wherein said contacting is carried out in the temperature range of about −80° to about 200° C. and in the pressure range of about 0 to about 2000 psig.

4. A process according to claim 3 wherein said monoolefin is propylene.

5. A process according to claim 4 wherein said contacting is carried out in the temperature range of about −10° to about 50° C. and in the pressure range of about 20 to about 50 psig.

6. A process according to claim 3 wherein said organoaluminum compound is methylaluminum sesquichloride.

* * * * *